US009785752B1

(12) United States Patent
Black et al.

(10) Patent No.: US 9,785,752 B1
(45) Date of Patent: Oct. 10, 2017

(54) METHOD FOR STRATIFYING AND SELECTING CANDIDATES FOR RECEIVING A SPECIFIC THERAPEUTIC APPROACH

(71) Applicant: Flagship Biosciences, Inc., Westminster, CO (US)

(72) Inventors: Joshua Black, Denver, CO (US); Carsten Schnatwinkel, Boulder, CO (US); Kristin Wilson, Denver, CO (US); Nathan T. Martin, Boulder, CO (US); Joseph Krueger, Andover, MA (US); Holger Lange, Enger (DE)

(73) Assignee: Flagship Biosciences, Inc., Westminster, CO (US)

( * ) Notice: Subject to any disclaimer, the term of this patent is extended or adjusted under 35 U.S.C. 154(b) by 0 days.

(21) Appl. No.: 14/986,512

(22) Filed: Dec. 31, 2015

Related U.S. Application Data (63) Continuation-in-part of application No. 14/189,864, filed on Feb. 25, 2014, now abandoned.

(51) Int. Cl.
*G06K 9/00* (2006.01)
*G06F 19/00* (2011.01)
*G06T 7/00* (2017.01)
*G06K 9/62* (2006.01)

(52) U.S. Cl.
CPC ....... *G06F 19/3481* (2013.01); *G06K 9/6212* (2013.01); *G06T 7/0012* (2013.01); *G06T 2207/20036* (2013.01); *G06T 2207/20076* (2013.01); *G06T 2207/20104* (2013.01); *G06T 2207/30024* (2013.01)

(58) Field of Classification Search
None
See application file for complete search history.

(56) References Cited

U.S. PATENT DOCUMENTS

| 8,885,913 B2 * | 11/2014 | Basiji | G01N 33/57492 356/326 |
| 2006/0078926 A1 * | 4/2006 | Marcelpoil | C12Q 1/6886 435/6.14 |
| 2013/0004965 A1 * | 1/2013 | Sherley | G01N 33/5073 435/7.4 |

(Continued)

*Primary Examiner* — Tahmina Ansari
(74) *Attorney, Agent, or Firm* — Coastal Patent Law Group, P.C.

(57) ABSTRACT

The disclosure concerns a method for patient stratification and selection of patients who are candidates for a specific therapy is described which is based on quantifying one or more digital image analysis feature distributions from stained tissue. The method extends beyond the abilities of a manual observer and a microscope, and generally comprises: acquiring digital images of stained tissue sections from patients submitted for evaluation, applying an algorithm process to said images with a computer to extract the morphometric and staining features of image pixels and tissue objects, deriving one or more distribution function for one or more image analysis features, calculating a summary statistic of the one or more distribution functions, and using said summary statistic along with an associated predefined patient stratification paradigm to separate a patient cohort into distinct strata which correspond to a decision to include or exclude a patient for a specific therapy.

15 Claims, 10 Drawing Sheets

(56) References Cited

U.S. PATENT DOCUMENTS

2014/0030729 A1* 1/2014 Basiji ............... G01N 33/57492
                                                    435/6.14
2015/0004630 A1* 1/2015 Lange ................ G01N 33/5005
                                                    435/7.21

* cited by examiner

METHOD FOR STRATIFYING AND SELECTING CANDIDATES FOR RECEIVING A SPECIFIC THERAPEUTIC APPROACH

CROSS-REFERENCE TO RELATED APPLICATIONS

This application is a continuation in part (CIP) of commonly owned U.S. Ser. No. 14/189,864, filed Feb. 25, 2014, titled "TISSUE ANALYSIS SCORING SCHEME BASED ON HISTOGRAM STATISTICS"; the contents of which are hereby incorporated by reference.

BACKGROUND

Field of the Invention

This application relates to methods for evaluating tissue image analysis feature distribution functions with the intent to stratify patient cohorts into two or more distinct categories of interest. More specifically, the method utilizes digital tissue image analysis to extract staining and morphometric features from images of stained tissue sections, quantifies the distribution of one or more image analysis feature, and applies a patient selection paradigm based on a comparison of the patient-specific image analysis feature distribution to a reference distribution or value to identify patients as candidates for a specific therapy.

Description of the Related Art

The majority of current in vitro diagnostic assays, laboratory developed tests, and research use only assays are based on measuring the staining intensity of biomarkers of interest, such as HER2. The biomarker is visualized by using antibodies, histologic dyes, or in situ hybridization probes to detect the biomarker of interest and detection reagents such as chromogenic and fluorescent stains or dyes. Typically, evaluation of the staining, as a surrogate for the biomarker, is assessed manually by a pathologist. In some instances, digital image analysis algorithms which are configured to mimic manual scoring paradigms can also be used to evaluate biomarker expression in tissue. In general, these approaches often condense, in an over simplified manner, the sometimes heterogeneous distribution of staining intensities into a single summary score for a tissue.

As an illustrative example, the H-Score paradigm consists of a pathologist assessing two different conditions in a given tissue to assign a score. The pathologist categorizes staining on a semi-quantitative scale of 0, 1, 2, and 3+(negative, low, medium, and high expression, respectively). In addition, the pathologist must assign the percentage of tissue or cells within the tissue that falls into each category, with all four categories adding to 100%. Finally, an H-score is calculated by multiplying the score category (i.e. 0, 1, 2, 3+) by the percentage of tissue (i.e. 0-100%) in that category and results in a score ranging from 0 to 300.

Interestingly, with the H-Score paradigm, two different tissues with unique staining distributions (e.g. one tissue with 100% of cells staining in the 1+ category and a second tissue with 50% of cells staining in the 0 and the other 50% of cells staining in the 2+ categories) can have the same H-score (e.g. an H-Score of 100 for both tissues), and illustrates the conundrum with present scoring paradigms which overly simplify complex staining information into a single summary score.

Alternatively, a tissue can be scored, as a whole, on a 0, 1, 2, and 3+ scale. This scoring approach assigns a score to a tissue based on the maximum staining level observed in a specified percentage of the tissue (e.g. strong staining in >15% of tumor cells scores a tissue sample as 3+). In this scoring paradigm, only the staining intensity of a subset of cells or tissue area is considered, and the information contained in the remainder of the tissue is discarded in the summary score.

While these scoring approaches have demonstrated utility for evaluating biomarkers, there are instances where the scoring paradigms are insufficient to capture the necessary granularity of biomarker expression to guide insights or patient selection decisions. Digital tissue image analysis has evolved into a powerful tool for extracting a great deal of information from stained tissue. Digital image analysis can quantify many features, both morphometric and staining, related to biomarker and tissue presentation for use in developing novel scoring paradigms.

SUMMARY

The disclosure concerns a novel tissue scoring methodology which utilizes digital image analysis of tissue to assess the full distribution of a morphometric and staining features in a way that categorizes samples based on summary values which better capture the nuanced nature of image analysis feature distributions.

In accordance with the embodiments herein, a novel method for patient stratification and selection of patients who are candidates for a specific therapy is described which is based on quantifying one or more digital image analysis feature distributions from stained tissue. The method extends beyond the abilities of a manual observer and a microscope, and generally comprises: acquiring digital images of stained tissue sections from patients submitted for evaluation, applying an algorithm process to said images with a computer to extract the morphometric and staining features of image pixels and tissue objects, deriving one or more distribution function for one or more image analysis features, calculating a summary statistic of the one or more distribution functions, and using said summary statistic along with an associated predefined patient stratification paradigm to separate a patient cohort into distinct strata which correspond to a decision to include or exclude a patient for a specific therapy.

BRIEF DESCRIPTION OF THE DRAWINGS

FIGS. 5(A-C) show an embodiment of this invention wherein the summary statistic of an image analysis feature distribution function, the cumulative distribution function in this example, is the area under the curve.

DETAILED DESCRIPTION OF EMBODIMENTS

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions without departing from the spirit and scope of the invention.

Figure 1:
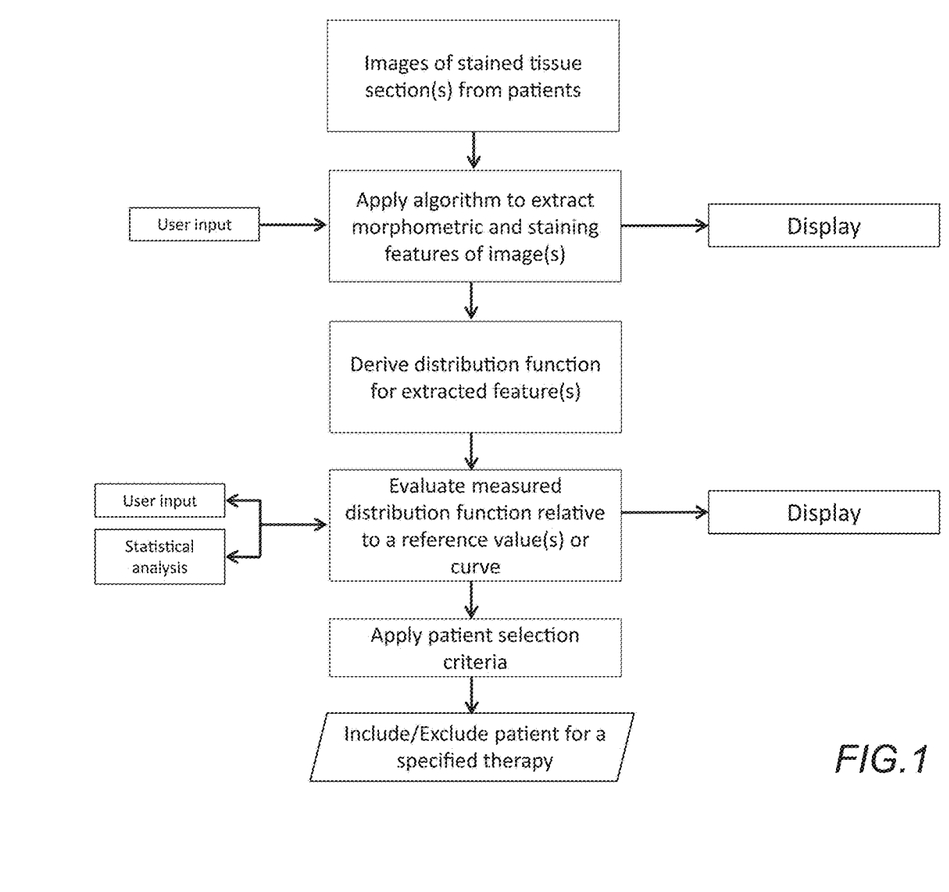
FIG. 1 depicts the preferred embodiment of this invention wherein the distribution function of an image analysis feature, extracted from an image of a stained tissue section with an algorithm process, is evaluated to determine whether to include or exclude a patient from a specific therapy.

In one embodiment, the method may be comprised of nine steps: 1) obtaining digital images of stained tissue sections; 2) extracting staining and morphometric features of cells or tissue structures within the image using a digital image analysis algorithm implemented by a computer; 3) storing image analysis feature values in computer memory or a database for future recall and processing; 4) calculating the probability density function or cumulative density function for one or more image analysis features; 5) deriving a summary score for the probability density function and cumulative density function; 6) evaluating the summary score(s) relative to reference value(s); 7) applying patient selection criteria to the evaluation of summary and reference values; 8) selecting or excluding patients for a particular therapy based on said patient selection criteria. FIG. 1 outlines one preferred embodiment of this invention.
Extraction of Cellular or Tissue Features by Applying an Algorithm Process The following method described in this invention is utilized to evaluate one or more patient tissue samples to determine whether or not said patient or patients are candidates for a specified therapy. To perform the following invention, digital images of stained tissue sections from the one or more patients are obtained.

Patient tissue samples for evaluation are generated using standard histologic processes to produce tissue sections mounted on glass histology slides. Each tissue section for a patient is stained to highlight expression of one or more biomarkers by one or more of: standard immunohistochemistry (IHC), in situ hybridization (ISH), histological stains (i.e. H&E, trichrome, etc.) and immunofluorescent (IF) methods to generate tissue stained in a manner to evaluate said biomarker. One or more biomarker may be stained for in each tissue section (i.e. mono- and multiplexed assay formats) or on multiple sections from a patient's tissue sample (e.g. one biomarker per serial section for a single patient).

Stained tissues mounted on histology slides are digitized using standard practices (i.e. digital slide scanning, imaging with a digital camera mounted on a microscope, etc.) for chromogenic and/or fluorescent stains. The digital images of each patient tissue sample are stored in computer memory or in a database for future recall and analysis. The images can be bright-field, dark-field, bright- or dark-field equivalent images, or a combination image of bright- and dark-field images.

The one or more patient sample cohort is submitted for evaluation by the following invention once digital images are available.

In the preferred embodiment of this invention, a digital tissue image analysis algorithm implemented by a computer is applied to each image to extract the morphometric and staining features pertaining to staining presentation in each image. Image analysis features can be extracted in pixel-based (e.g. per-pixel staining intensity for biomarker staining color) or object-based (e.g. staining intensity for a biomarker staining color within identified cells) manner.

Morphometric features pertain to the size, shape, and texture of tissue stains within objects (i.e. cells, cell membranes, blood vessels, tumor epithelium regions, etc.) observed in a digital image. For example and not limitation, morphometric features can be the area of a cell nucleus, the completeness of biomarker staining in a cell membrane, the diameter of a cell nucleus, the roundness of a blood vessel etc. Staining features pertain to the pixel intensities of specified IHC, ISH, and IF stains or dyes. Staining features can be evaluated relative to objects (e.g. average staining intensity in each cell in an image) or relative to individual pixels across an image (e.g. average staining intensity of pixels in a sample).

The image analysis algorithm implemented by a computer captures morphometric and staining features for each pixel and/or object within an image and stores said values for further analysis in computer memory or to a database.

Figure 2:
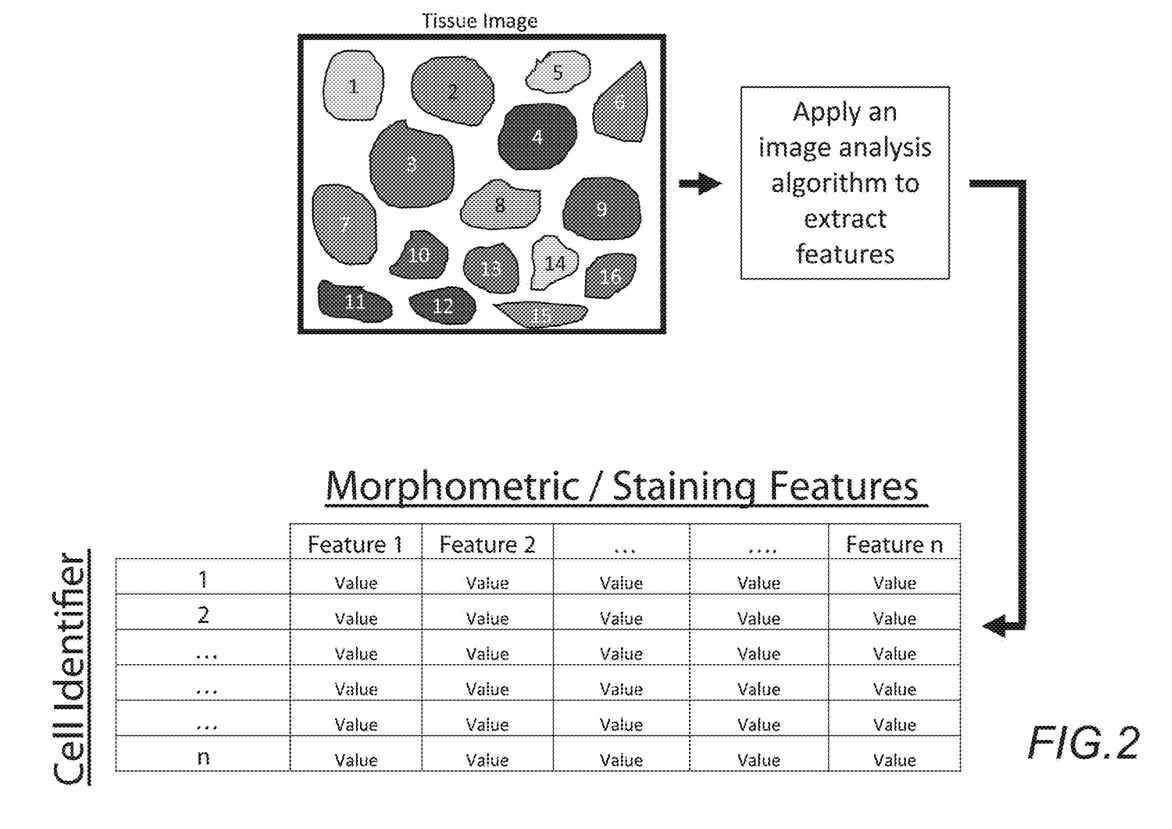
FIG. 2 illustrates the process by which the algorithm process applied by a computer extracts features from a digital image of a stained tissue section to transform the tissue image into numerical data related to staining and object presentation in the tissue.

For example and not limitation, FIG. 2 depicts a tissue image field wherein a number of image objects (e.g. cells) are identified within an image and are illustrated by the numbered objects within the FIG. For a given morphometric or staining feature, each image object is characterized by a unique value corresponding to the presentation of histologic stains which is depicted by the range of greyscale object fill color. The image analysis algorithm implemented by a computer extracts said features and stores the values for each image object (i.e. cells, pixels, blood vessels, etc.) for future recall and analysis.
Quantify Patient-Specific Distributions of Image Analysis Features:

In the preferred embodiment of this invention, the probability density function (PDF) or cumulative distribution function (CDF) is calculated using standard approaches for one or more selected image analysis feature. Capture of the PDF or CDF for an image analysis feature goes far beyond current tissue scoring paradigms by retaining the complete information of staining or morphometric feature distribution for pixels or objects identified within an image of a stained tissue section. Furthermore, summary statistics of either the PDF or CDF's for an image analysis feature retain greater information about the image analysis feature than existing paradigms.

Figure 3:
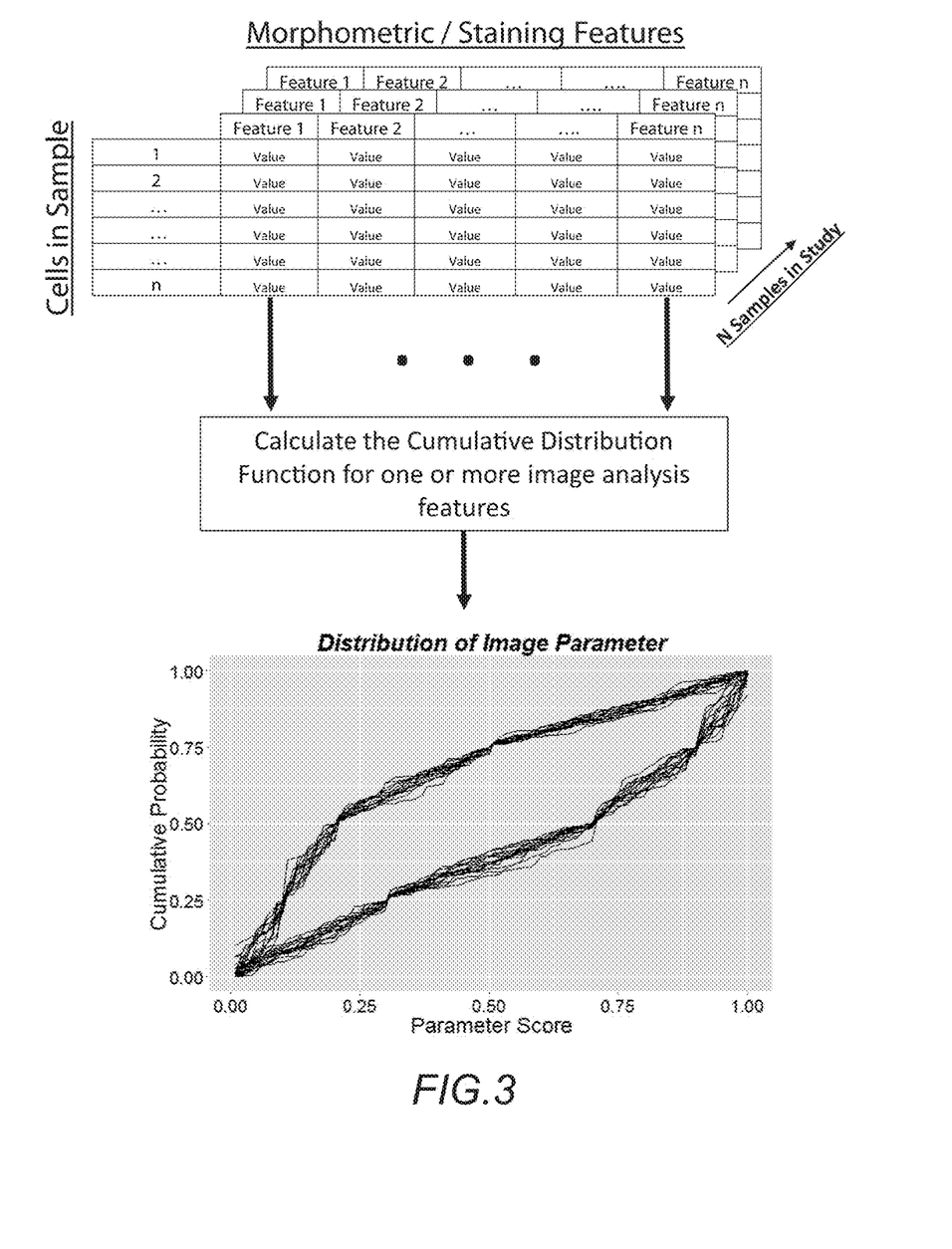
FIG. 3 demonstrates calculating an image analysis feature distribution function for one or more image analysis features for a patient cohort to use in further evaluation and graphic display.

In an illustrative example, FIG. 3 demonstrates the derivation of the CDF for one or more image analysis features from the cells identified within an image for a study cohort. For the one or more image analysis features evaluated in each cell in an image, the distribution of said one or more features is evaluated. From the distribution of feature values, the CDF is derived for each patient sample and can be visualized on a plot to determine differences in feature distribution across a tissue cohort which would not be apparent by current tissue scoring paradigms.

The CDF and PDF functions quantify the entire distribution of an image analysis feature (e.g. biomarker staining intensity from 0% to 100% of the possible dynamic range of the feature) in a standardized way that allows comparisons between distributions. Once the CDF and PDF are derived for an image analysis feature in each patient sample, summary statistics can be determined for either distribution. Similarly, a sub-range (i.e. biomarker staining intensity ranging from 0% to 50% of maximum, biomarker staining intensity ranging from 20% to 60% of the possible dynamic range, etc.) of the CDF and PDF can be evaluated and summary statistics can be calculated for the sub-range only.

PDF summary statistics are histogram statistics and can be one or more of: mean, median, mode, minimum, maximum, standard deviation of the mean, standard error of the mean, skewness, density at a specified point (e.g. 50% biomarker staining), full-width at half maximum, number of resolvable peaks, and kurtosis values. CDF summary statistics can be one or more of: the area under the curve (AUC), the slope of the curve, the slope over a defined range of the curve, the difference in image analysis parameter values between two defined cumulative distribution values, the difference in cumulative distribution values between two image analysis parameter values, the point of maximum deviation from a reference curve, and the sum of residuals or squared residuals (deviations) from a reference curve.

Summary statistics for both the PDF and CDF can be calculated for the entire range (e.g. feature value of 0 to the maximum possible dynamic range value) of a feature or for a defined sub-range (e.g. 20% to 60% of the possible dynamic range maximum value). In the instance where a sub-range is assessed, the AUC can be determined for a PDF as a summary statistic.

Figure 4:
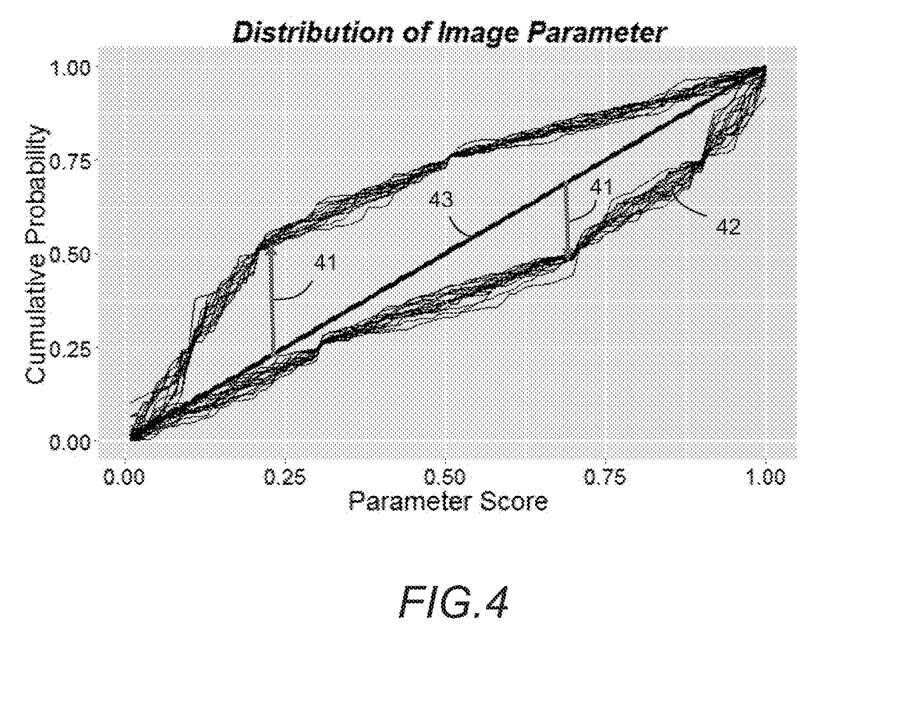
FIG. 4 illustrates an embodiment of this invention wherein the summary statistic of an image analysis feature distribution function is the point of maximum distance (greyscale arrows) to a reference curve (heavy black line).

FIG. 4 demonstrates summarizing CDF functions for a cohort of patients using the point of maximum deviation 41 from a reference CDF. The point of maximum deviation 41 is highlighted for each group of curves 42 (thin black lines) by a grey arrow indicating the point and distance to the reference curve 43 (thick black line).

Figure 5A:
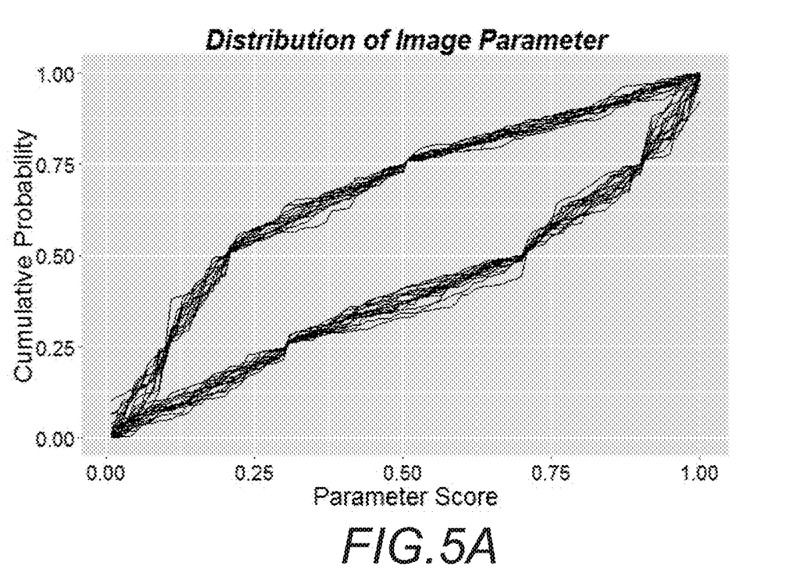
Figure 5B:
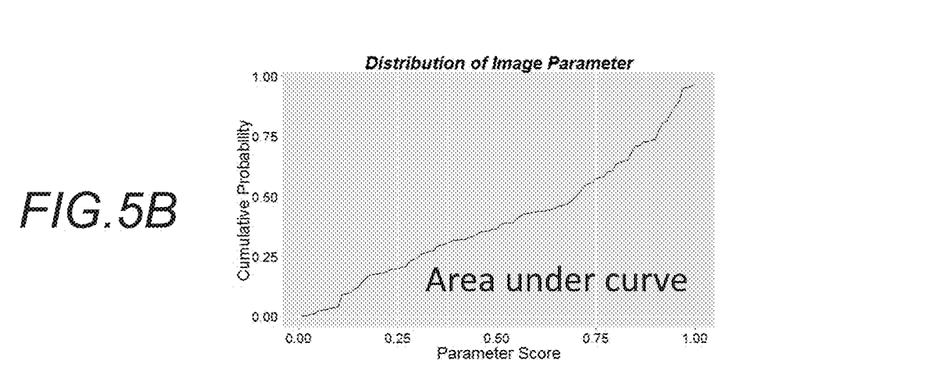
Figure 5C:
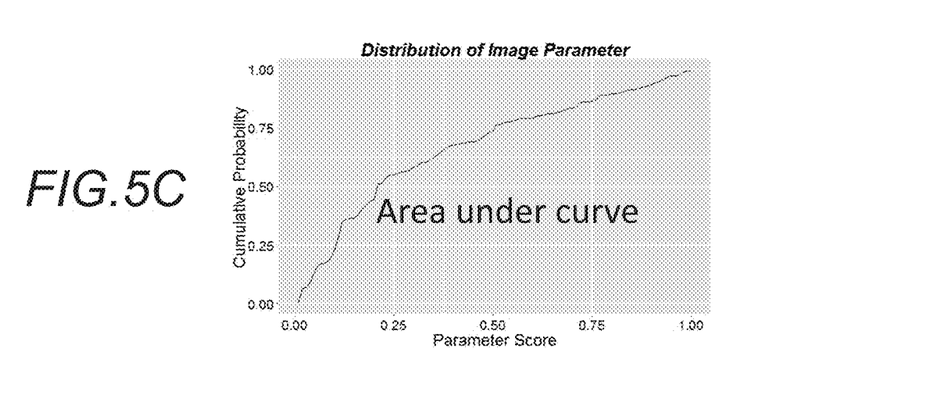

FIGS. 5(A-C) demonstrate summarizing CDF functions for a cohort of patients using the area under the curve value. FIG. 5A illustrates the different CDFs of an image analysis feature for a patient cohort. FIGS. 5 B and C illustrate two cases from the cohort of patients with different CDFs for an image analysis feature and qualitatively demonstrate the difference in areas under the curve for the two cases.

Figure 6:
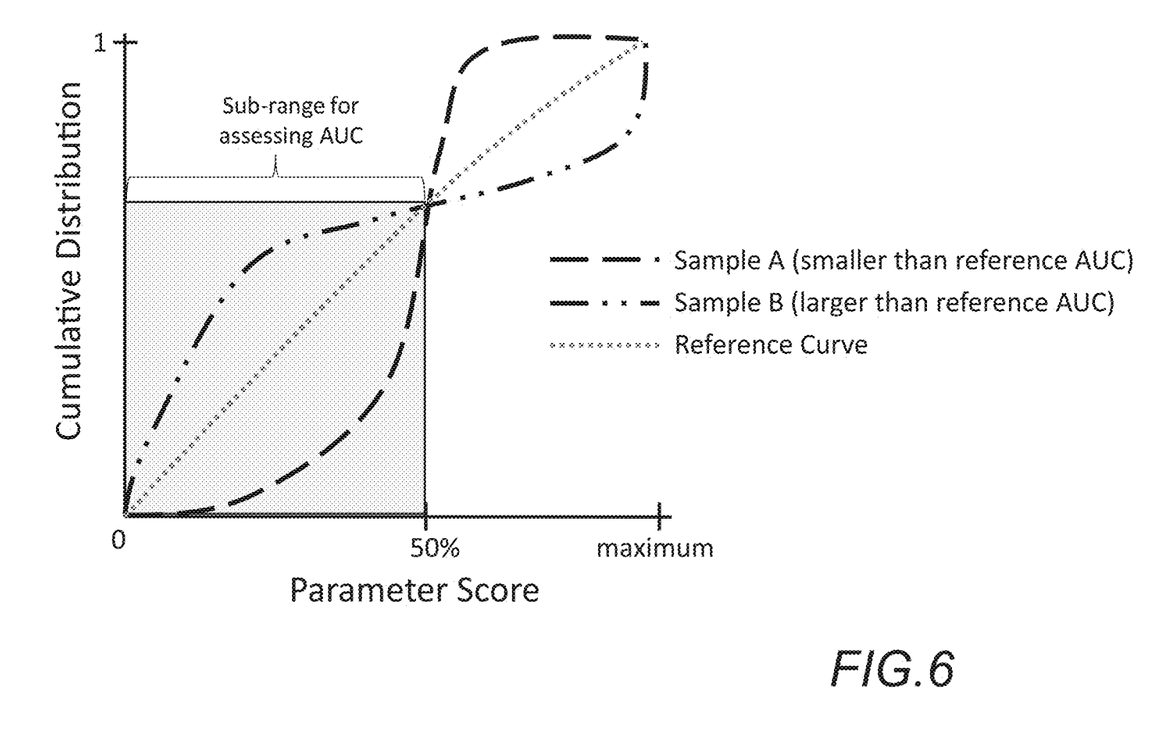
FIG. 6 illustrates an embodiment of this invention wherein the summary statistic of the cumulative distribution function for an image analysis feature is calculated only over a sub-range of feature values to determine two patient summary values (area under the curve, AUC) relative to a reference curve.

FIG. 6 illustrates an example case where it might be advantageous to calculate a summary statistic for a CDF function over a sub-range of image analysis feature values. In this instance, the shape of the CDF function for two different patients crosses the reference curve in multiple locations. Evaluation of the CDF summary statistic (AUC) in a defined range where the key biologic information is capture enables an interpretable summary statistic for the samples.

Figure 7:
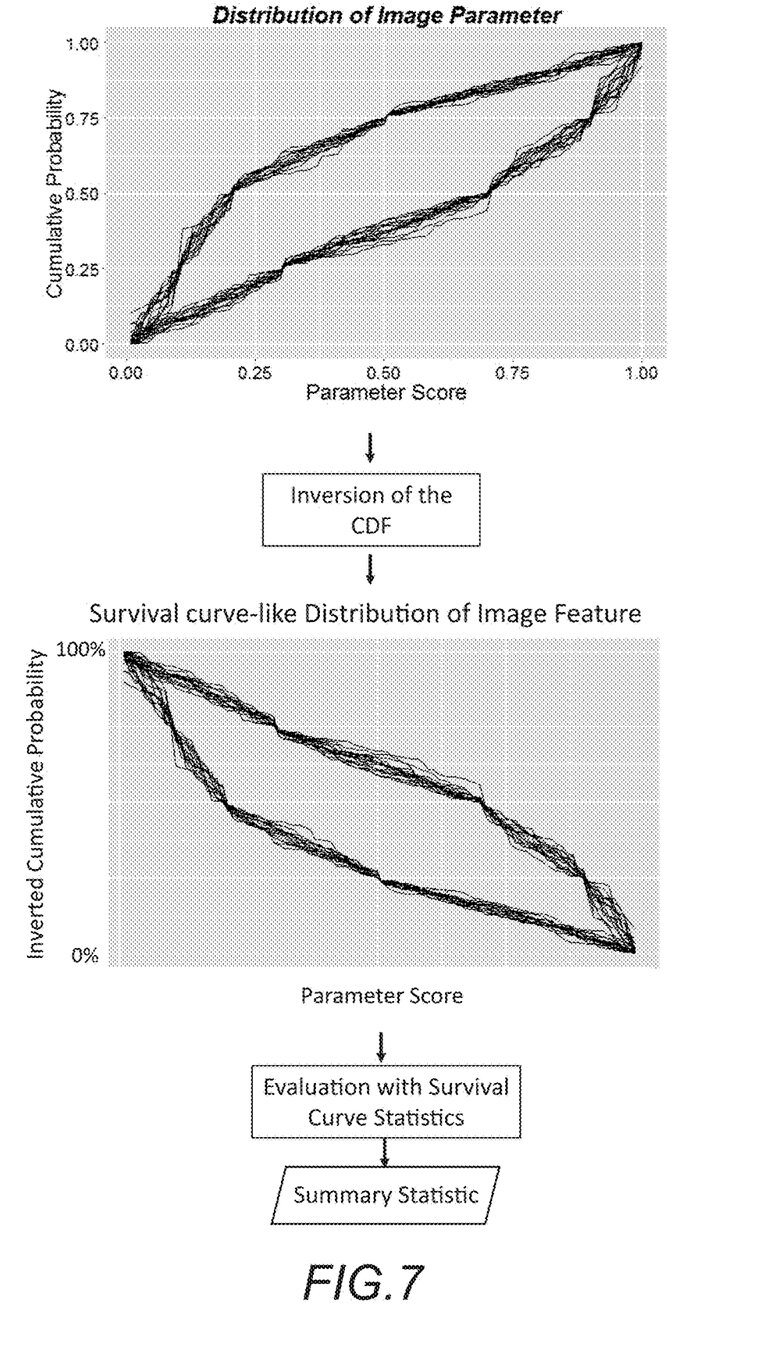
FIG. 7 illustrates an embodiment of this invention wherein the cumulative distribution function of an image analysis feature is transformed through inverting the curve to produce a survival curve-like dataset which can be evaluated using survival curve statistics.

In an embodiment of the present invention, survival curve statistics can be utilized to determine a summary score for the distribution of an image analysis feature for a patient cohort. In this embodiment, the CDF is transformed (e.g. inverted) to generate a survival curve-like representation of the image analysis feature distribution. Once transformed, survival curve evaluation statistics can be derived which summarize the nature of the distribution or compare a patient-specific distribution to a reference curve. FIG. 7 illustrates the method by which the CDF for a patient cohort is transformed to evaluate an image analysis feature distribution utilizing survival curve evaluation statistics.

Stratifying Patients Based on Image Analysis Feature Distribution Summary Statistics:

In the preferred embodiment of the present invention, the summary statistic(s) derived from the PDF or CDF for one or more image analysis features are utilized to stratify patients into two or more groups for selection/exclusion as candidates for a specified therapy. The patient selection criteria will be pre-defined criteria which can be applied to a patient cohort to stratify patients into one or more groups selected to receive a therapy and one or more groups which are excluded from receiving a therapy.

In one embodiment of this invention, image analysis evaluation of one biomarker is used to determine a summary score for patient selection. In another embodiment of this invention, image analysis is utilized to evaluate multiple biomarkers to derive a summary score for use in patient selection.

Figure 8:
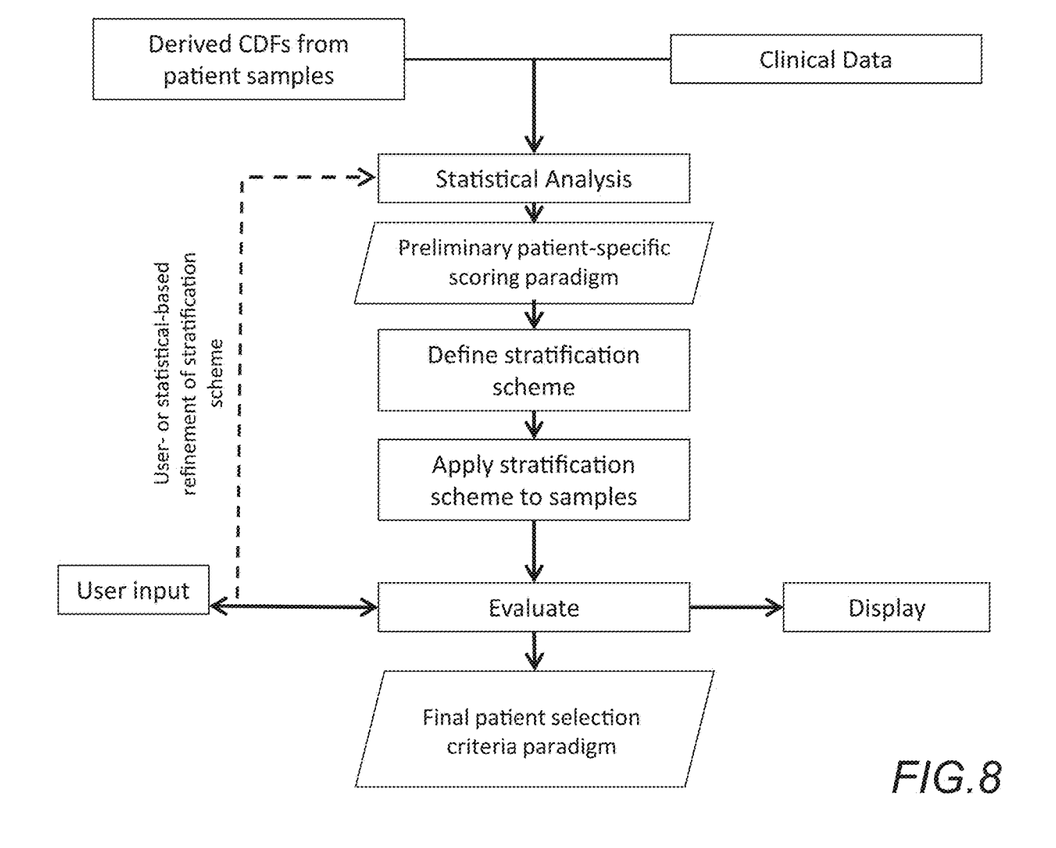
FIG. 8 provides an example process by which patient selection criteria and a patient selection paradigm is derived for use with the method encompassed by the present invention.

FIG. 8 provides an illustrative, and not limiting, example of the process by which a patient selection criteria paradigm is determined. In this example, the CDF for an image analysis feature is derived for each patient and combined with clinical data (e.g. survival) for a single biomarker. These data are evaluated with standard statistical analysis methods to identify a preliminary patient specific scoring paradigm which identifies the optimal summary statistic for the CDF relative to patient stratification. Using the selected summary statistic, patient stratification and selection criteria are defined, reviewed, and finalized to define the patient selection criteria paradigm.

Figure 9:
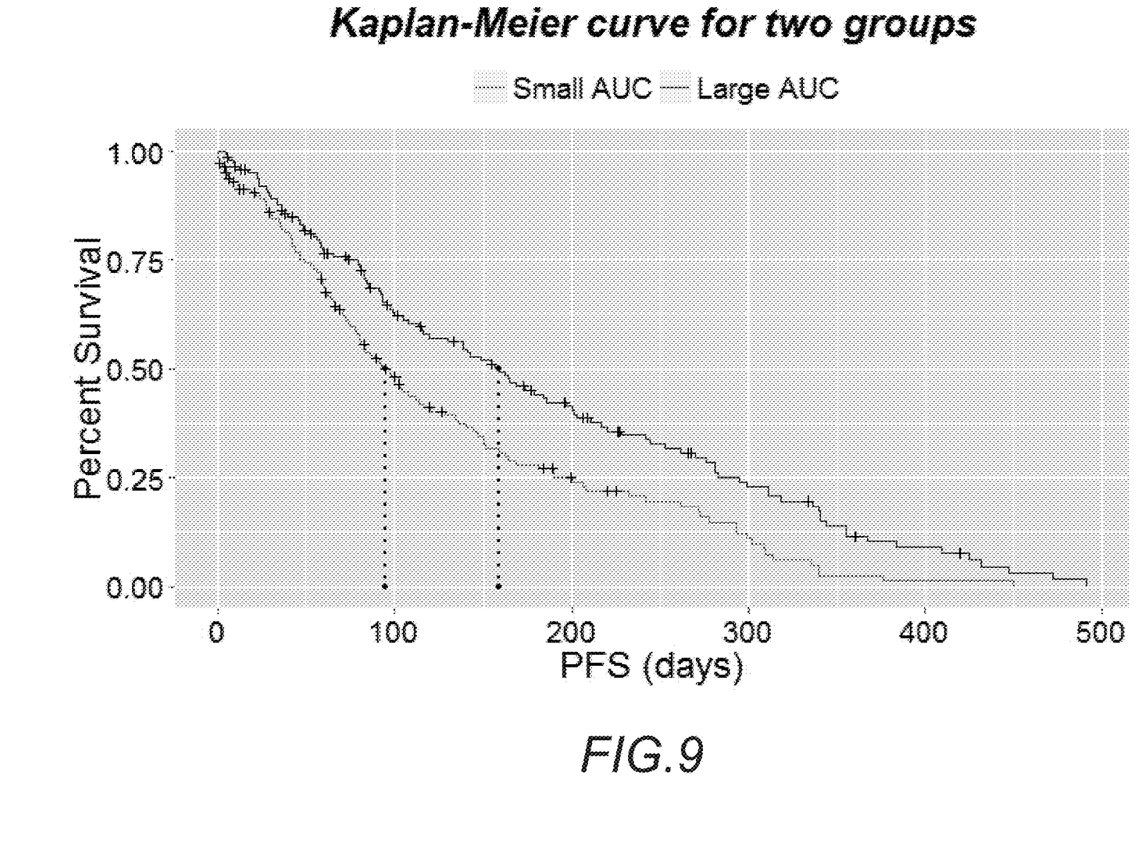
FIG. 9 provides an illustrative example of patient outcome data stratified by the area under the curve (AUC) summary statistic for an image analysis feature cumulative distribution function and demonstrates a survival benefit for patients with large AUC.

FIG. 9 provides an example wherein a patient cohort is stratified based on the area under the curve (AUC) summary statistic for an image analysis feature and evaluated relative to patient outcome data such as progression free survival (PFS). In this example, patients with a larger AUC value have improved median PFS when compared with patients who have a smaller AUC value. In this example, a patient selection criteria would be defined to stratify patients into large and small AUC groups, wherein the large AUC group would be identified to have a better outcome for a given therapeutic.

The patient selection criteria paradigm can rely on one or more image analysis feature and summary statistic of said feature distributions within samples for a patient cohort. The patient selection criteria paradigm can rely on summary statistics information for image analysis features from a single biomarker or multiple biomarkers.

Once the patient selection criteria paradigm is identified, the method described herein is applied to a patient cohort submitted for evaluation. In the preferred embodiment of this invention, the extracted image analysis features for the patient cohort which are relevant to the defined patient selection paradigm are collected and one or more of the:

PDF, CDF, and inverted CDF is derived. Statistical analysis is used to derive one or more relevant summary statistic for the image analysis feature distribution for each patient and pre-defined patient selection criteria are applied to stratify the patient cohort into distinct strata. The patient selection criteria will stratify patients into two or more groups which have previously been determined to correspond to a treatment approach.

Figure 10:
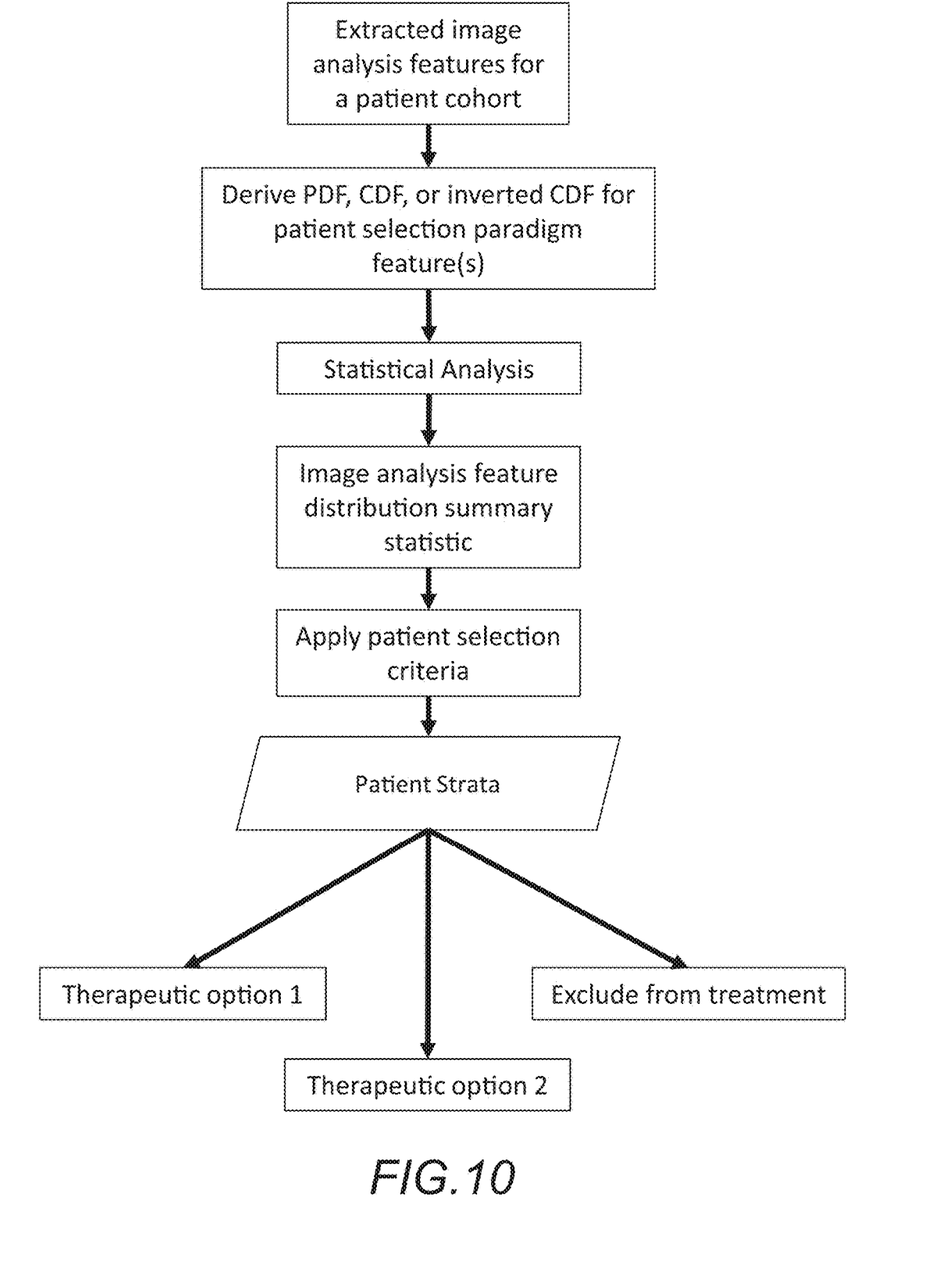
FIG. 10 illustrates the preferred embodiment of this invention wherein a summary statistic for a distribution function of an extracted image analysis feature is evaluated relative to patient selection criteria to identify patient strata which are associated with inclusion or exclusion decision for a specific therapy.

FIG. 10 illustrates this embodiment of the present invention wherein the above mentioned steps are applied to a patient cohort to select patients for a specific therapy. In this example, the patient selection criteria separate patients into three strata which correspond to inclusion for one of two therapies or exclusion from treatment with either therapy. In the preferred embodiment of this invention, the stratification criteria can stratify patients into two strata (e.g. include for treatment and exclude from treatment) or a plurality of strata (e.g. include for treatment A, include for treatment B, include for treatment C, etc.).

What is claimed is:

1. A method or stratifying and selecting candidates for receiving a specific therapeutic approach, the method comprising: a. obtaining digital images of stained tissue sections mounted on glass slides; b. identifying one or more regions of analysis (ROAs); c. extracting data associated with one or more staining and morphometric features, said features including one or more of: image pixels, cell objects, and tissue structure objects within each digital image, wherein said extracting includes applying a digital image analysis algorithm process implemented by a computer for each image; d. storing the data for each cell or tissue structure in computer memory or a database; e. visualizing the distribution of one or more of the staining or morphometric feature data analyzed by the algorithm process implemented by the computer; f. calculating a function which captures the distribution of data for one or more staining or morphometric features for all of the analyzed pixels, cells objects or tissue structure objects within one of the ROAs; g. deriving a summary score for the function which captures the distribution for said one or more staining or morphometric features; h. evaluating said summary score relative to one or more pre-defined reference values and associated patient stratification and selection criteria; and i. selecting a patient as a candidate for a specified therapy based on said evaluation of a summary score value relative to the reference values and accompanying selection criteria, wherein the tissue is stained for a single biomarker or multiple biomarkers within the same tissue section or in multiple tissue sections from the same patient and wherein the morphometric and staining features are evaluated by the algorithm process in an object-based or pixel-based manner.

2. The method of claim 1, wherein the tissue is stained using one or more of: immunohistochemistry, histological dyes, immunofluorescence, and in situ hybridization prior to digitization.

3. The method of claim 1, wherein the morphometric features characterize physical presentation of cell compartments, tissue compartments and tissue structures in a tissue and relate to physical measures of size, shape, texture, and quantity thereof.

4. The method of claim 1, wherein staining features relate to the presentation of tissue stains within defined cell compartments, tissue compartments and tissue structures and relate to staining intensity and staining completeness.

5. The method of claim 1, wherein the function which captures the distribution of morphometric or staining features is one or more of: a histogram distribution, probability distribution function, cumulative distribution function, and inverted cumulative distribution function.

6. The method of claim 5, wherein the distribution function for a given parameter is visualized graphically through a graphical user interface.

7. The method of claim 5, wherein the summary score describing the histogram distribution or probability density function is one or more of: minimum, maximum, mean, median, mode, skewness, kurtosis, full-width at half maximum, number of resolvable peaks, area under the curve, and normalness value.

8. The method of claim 5, wherein the summary score describing the cumulative density function is one or more of: an area under the curve (AUC), slope of the curve, slope over a defined range of the curve, difference in image analysis parameter values between two defined cumulative distribution values, difference in cumulative distribution values between two image analysis parameter values, point of maximum deviation from a reference curve, and sum of residuals or squared residuals from a reference curve.

9. The method of claim 7, wherein the summary score describing histogram, probability density, and cumulative distributions can be derived over one or more of: a measured dynamic range of image analysis feature values, possible dynamic range of an image analysis feature, and a sub-range of image analysis feature values.

10. The method of claim 1, wherein the summary score describing the inverted cumulative density function includes one or more Kaplan-Meier statistics values.

11. The method of claim 1, wherein the summary score for one or more distributions is evaluated relative to one or more matched reference values and associated patient stratification criteria.

12. The method of claim 11, wherein the one or more summary scores can be derived from: one distribution, multiple distributions describing a single biomarker, or multiple distributions describing multiple biomarkers.

13. The method of claim 11, wherein the patient stratification criteria define two or more patient strata based on one or more reference values.

14. The method of claim 12, wherein one or more patient strata are linked to positive response to one or more specified therapy.

15. The method of claim 1, wherein patients are selected or excluded from a specific therapy based on their membership to a specific strata determined by the patient stratification and selection paradigm.

* * * * *